US00PP31291P2

(12) United States Plant Patent
Sills et al.

(10) Patent No.: US PP31,291 P2
(45) Date of Patent: Dec. 31, 2019

(54) BLACKBERRY PLANT NAMED 'DRISBLACKSEVENTEEN'

(50) Latin Name: ***Rubus* L. subgenus *Rubus***
Varietal Denomination: DrisBlackSeventeen

(71) Applicant: Driscoll's, Inc., Watsonville, CA (US)

(72) Inventors: Gavin R. Sills, Gilroy, CA (US); Mark F. Crusha, Capitola, CA (US); Missael Bonifacio Romero Escobedo, Ciudad Guzmán (MX); Andrea M. Pabon, Gilroy, CA (US); Jorge Rodriguez Alcazar, Texcoco (MX)

(73) Assignee: Driscoll's, Inc., Watsonville ( * ) Notice: Subject to any disclaimer, the term of this patent is extended or adjusted under 35 U.S.C. 154(b) by 0 days.

(21) Appl. No.: 15/932,943

(22) Filed: May 24, 2018

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear |
| PP13,758 | P3 | 5/2003 | Fear |
| PP13,759 | P3 | 5/2003 | Fear |
| PP14,682 | P3 | 4/2004 | Fear |
| PP14,765 | P2 | 5/2004 | Fear et al. |
| PP14,780 | P2 | 5/2004 | Fear et al. |
| PP15,058 | P2 | 8/2004 | Fear et al. |
| PP17,162 | P3 | 10/2006 | Clark et al. |
| PP17,983 | P2 | 9/2007 | Cabrera Avalos |
| PP22,002 | P2 | 7/2011 | Sills et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Sills et al. |
| PP24,701 | P3 | 7/2014 | Sills et al. |
| PP24,878 | P2 | 9/2014 | Sills et al. |
| PP25,502 | P3 | 5/2015 | Sills et al. |
| PP26,501 | P3 | 3/2016 | Sills et al. |
| PP26,611 | P3 | 4/2016 | Sills et al. |
| PP26,774 | P3 | 5/2016 | Sills et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |

OTHER PUBLICATIONS

Voss, Donald H. "The Royal Horticultural Society Colour Chart 2001", Journal American Rhododendron Society, vol. 56, No. 1, 2002, 3 pages.

Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Anne Marie Grunberg
(74) *Attorney, Agent, or Firm* — Morrison & Foerster LLP

(57) ABSTRACT

A new and distinct variety of blackberry plant named 'DrisBlackSeventeen', particularly characterized by its high yield potential and high vigor, is disclosed.

4 Drawing Sheets

Latin name: Botanical classification: *Rubus* L. subgenus *Rubus*.

Varietal denomination: The varietal denomination of the claimed variety of blackberry plant is 'DrisBlackSeventeen'.

BACKGROUND OF THE INVENTION

Blackberry is the common name for a multitude of plant species bearing dark purple to black aggregate fruit in the genus *Rubus* of the family Rosacea. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K, Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of 3-6 m a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed by the University of Arkansas capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackSeventeen'.

Blackberry plant variety 'DrisBlackSeventeen' was discovered in Ventura County, Calif. on Feb. 27, 2009 and originated from a cross between the proprietary female parent blackberry plant 'BJ106.3' (unpatented) and the proprietary male parent blackberry plant 'Bulk A' (unpatented), The original seedling of the new variety was first asexually propagated via root cuttings in Santa Cruz County, Calif. in October of 2009.

'DrisBlackSeventeen' was subsequently asexually propagated via root cuttings, and underwent further testing at a farm in Michoacán, Mexico for five years (2012 to 2016). The present variety has been found to be stable and reproduce true to type through successive asexual propagations via root cuttings.

'DrisBiackSeventeen' exhibits the following distinguishing characteristics when grown under normal horticultural practices in Michoacán, Mexico:

1. High yield potential; and
2. High vigor.

'DrisBlackSeventeen' was selected for its flavor, fruit size, and adaptability to Central Mexico.

BRIEF DESCRIPTION OF THE DRAWINGS

This new blackberry plant is illustrated by the accompanying photographs, which show a cane, a leaf, flowers, and fruit of the plant. The colors shown are as true as can be reasonably obtained by conventional photographic procedures. The photographs are of plants that are three years old.

DETAILED BOTANICAL DESCRIPTION

Figure 1:
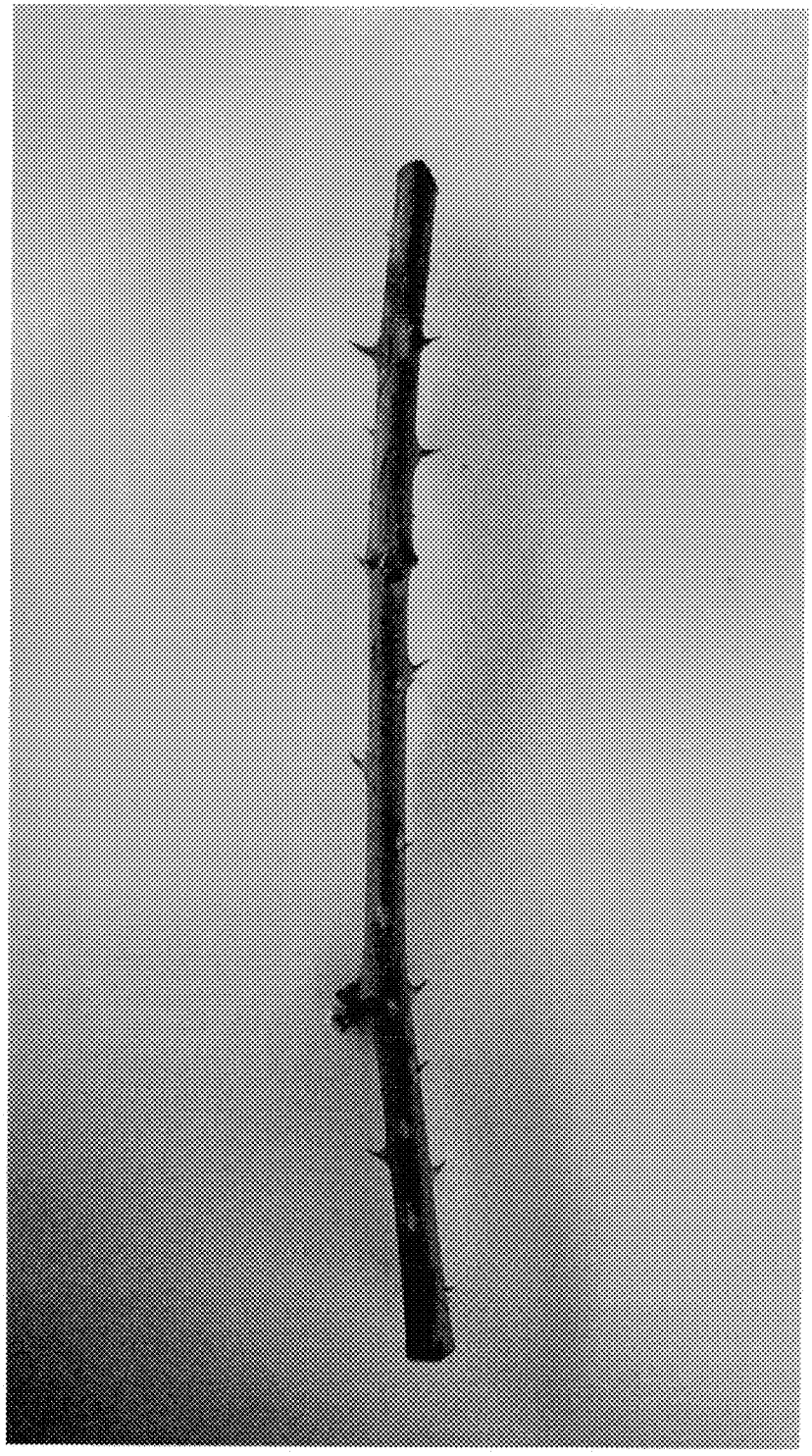
FIG. 1 illustrates a section of a cane of variety 'DrisBlackSeventeen'.
Figure 2:
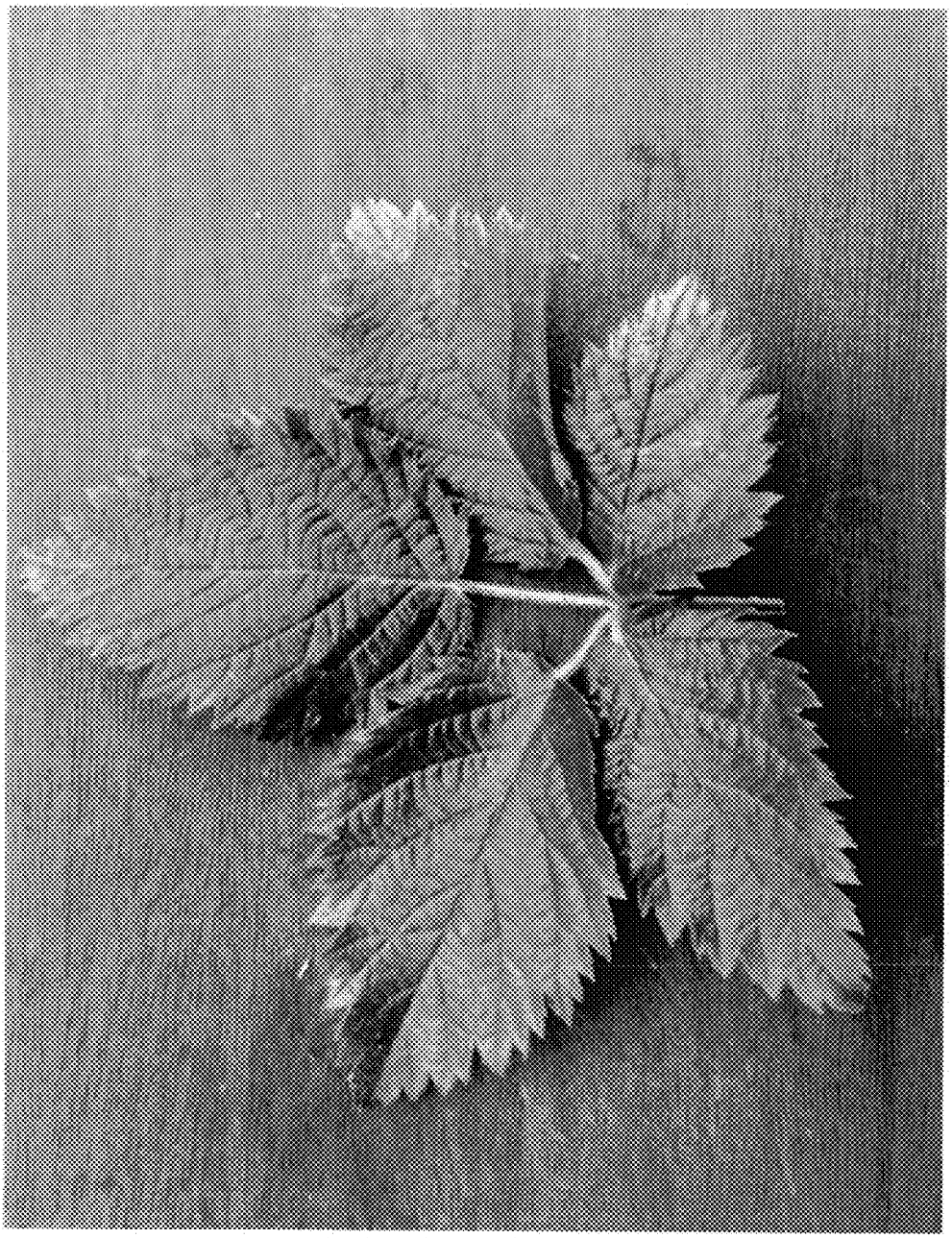
FIG. 2 illustrates a typical leaf of variety 'DrisBlackSeventeen'.
Figure 3:
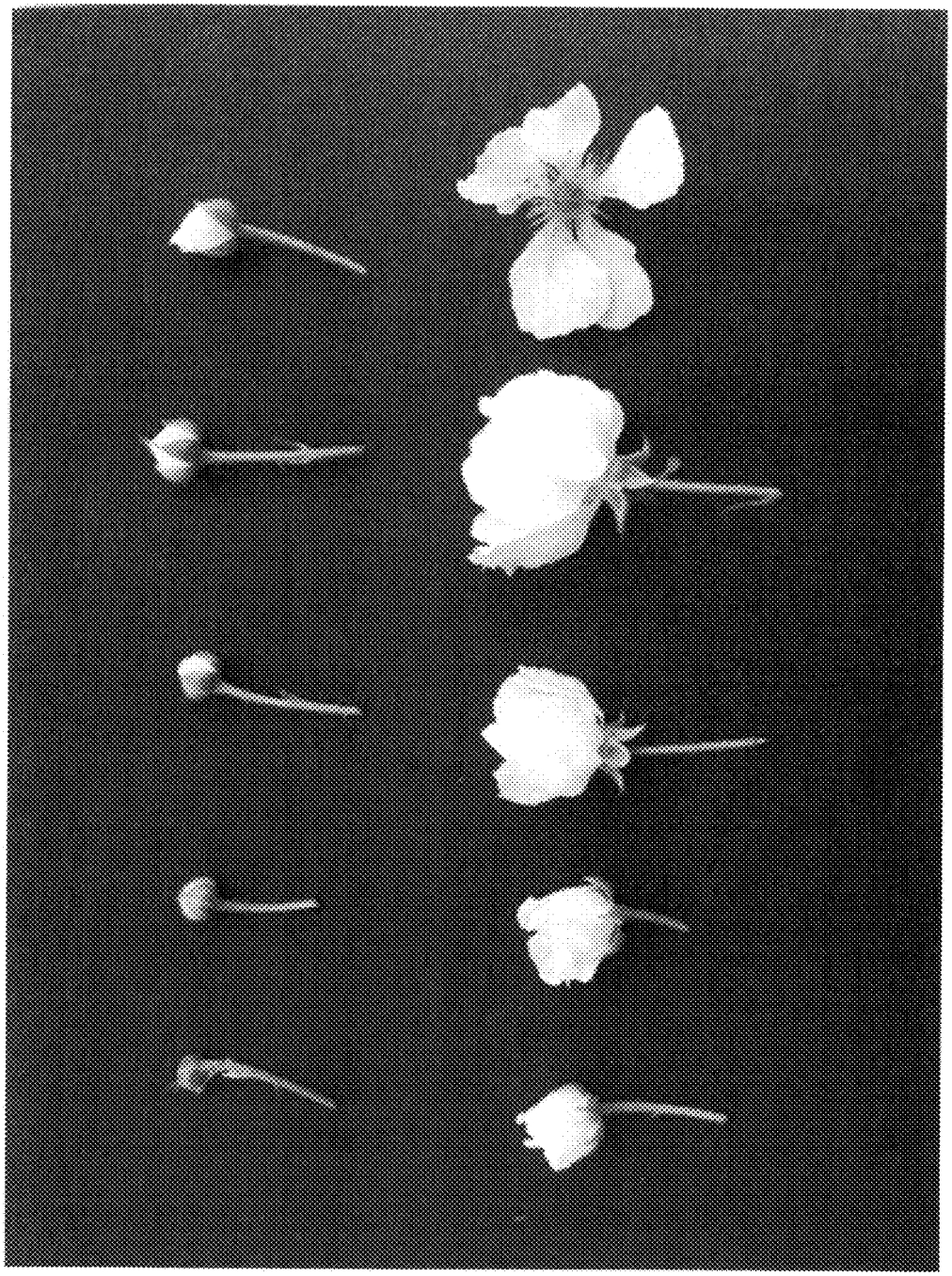
FIG. 3 illustrates typical flowers of variety 'DrisBlackSeventeen' at various stages of development.
Figure 4:
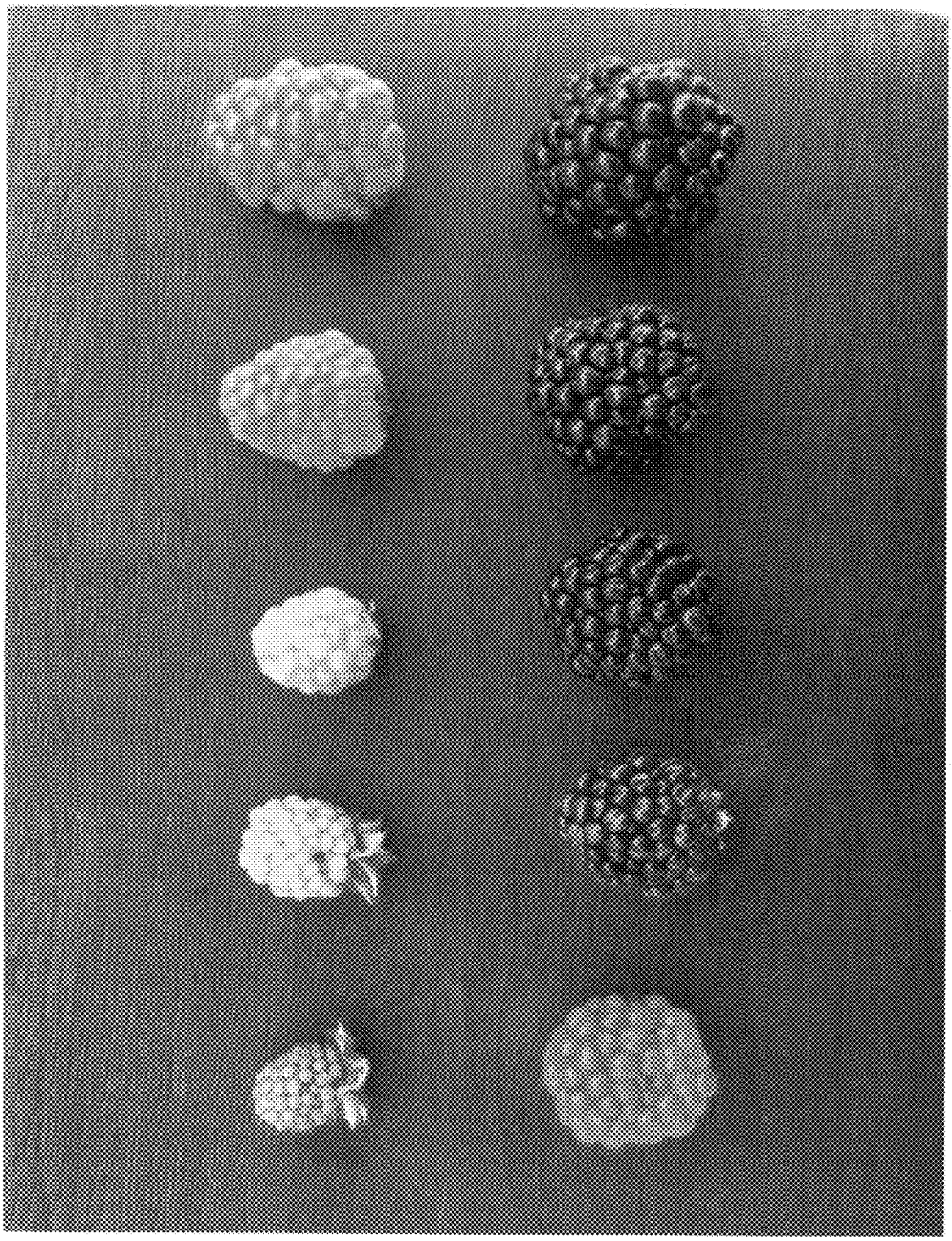
FIG. 4 illustrates typical fruit of variety 'DrisBlackSeventeen' at various stages of development.

The following descriptions set forth the distinctive characteristics of 'DrisBlackSeventeen'. The data that define these characteristics are based on observations taken in Michoacán, Mexico from 2012 to 2016. This description is in accordance with UPOV terminology. Color designations, color descriptions, and other phenotypical descriptions may deviate from the stated values and descriptions depending upon variation in environmental, seasonal, climatic and cultural conditions. 'DrisBlackSeventeen' has not been observed under all possible environmental conditions. The botanical description of 'DrisBlackSeventeen' was taken from three-year-old plants. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rosaceae.

*Botanical*.—*Rubus* L. subgenus *Rubus*.

*Common name*.—Blackberry.

*Variety name*.—'DrisBlackSeventeen'.

Parentage:

*Female parent*.—'BJ106.3' (unpatented).

*Male parent*.—'Bulk A' (unpatented).

Plant:

*Propagation*.—Root cuttings.

*Growth habit*.—Semi-upright.

*Number of new canes that develop each season*.—10-12.

Canes:

*Fruiting lateral length* (4$^{th}$ *lateral from tip*).—48.0 cm.

*Number of fruits per fruiting lateral*.—20.

*Internodal distance*.—5.2 cm.

*Dormant cane*.—Anthocyanin coloration: RHS 171B (Brownish orange). Predominant distribution of branches: Only on upper half. Cross-section: Rounded to angular.

Spines:

*Presence on dormant canes*.—Present.

*Attitude of apex in relation to cane*.—Upwards.

*Number of spines per particular area*.—6 per cm$^2$.

*Spine length*.—6.12 mm.

*Spine width at base*.—1.26 mm.

*Spine color*.—RHS 144A (Strong yellow-green).

Young shoots:

*Anthocyanin coloration* (*during rapid growth*).—RHS 173B (Moderate reddish orange).

*Intensity of green color*.—RHS 144A (Strong yellow-green).

*Density of glandular hairs per young shoot*.—Many.

Leaves:

*Terminal leaflet*.—Length: 75.45 mm. Width: 64.65 mm. Length/width ratio: 1.16. Lobing: Absent. Shape in cross-section: V-shaped. Undulation of margin: Weak. Presence of terminal leaflet blistering between veins: Present.

*Lateral leaflets* (*basal pair*).—Length: 56.20 mm. Width: 42.44 mm. Length/width ratio: 1.32.

*Rachis length between terminal leaflet and adjacent lateral leaflets*.—27.60 mm.

*Petiole*.—Length: 12.42 mm. Diameter: 0.52 mm.

*Leaflet*.—Type of incision of margin: Bi-serrate. Depth of leaflet incisions: 4.92 mm.

*Leaf*.—Predominant number of leaflets: 5. Type: Palmate. Intensity of green color of upper side: RHS 137A (Moderate olive green).

*Stipule*.—Stipule length: 11.24 mm. Stipule width: 1.45 mm.

*Time of leaf bud burst*.—September to October.

Flowers:

*Diameter*.—42.224 mm.

*Petal*.—Length: 21.16 mm. Width: 14.86 mm. Length/width ratio: 1.42. Color: RHS 155B (Yellowish white).

*Number of flowers observed at* $3^{rd}$ *node from tip of lateral*.—5.

*Pedicel*.—Length: 36.29 mm. Diameter: 0.265 mm.

*Time of flowering*.—October to November.

Fruit:

*Length of mature fruit*.—30.94 mm.

*Diameter of mature fruit*.—27.68 mm.

*Ratio of length to width*.—1.1.

*Drupelet*.—Drupelet diameter: 5.1 mm. Number of drupelets per fruit: 90.

*Shape in longitudinal section*.—Medium ovate.

*Color*.—RHS 202A (Dark greyish purple).

*Soluble solids* (*as degrees Brix*).—11.7° Bx.

*Acidity* (*as % citric acid*).—1.37%.

*Fruiting on current year's cane*.—Absent.

*Time of fruit ripening*.—December to January.

*Yield*.—12,600 kg/acre to 15,153 kg/acre of fruit per season from 48-month-old plants when grown in Santa Cruz County, Calif.

Resistance to diseases, pests, and abiotic stress:

*Fusarium wilt* (*Fusariun oxysporum*).—Moderately susceptible.

*Redberry mite* (*Acalitus essigi*).—Moderately susceptible.

*Drought*.—Moderately resistant.

*High temperatures*.—Resistant.

*Waterlogging*.—Resistant.

COMPARISONS TO PARENTAL AND COMMERCIAL BLACKBERRY VARIETIES

'DrisBlackSeventeen' differs from the proprietary female parent 'BJ106.3' (unpatented) in that 'DrisBlackSeventeen' has a higher yield potential compared to 'BJ106.3'.

'DrisBlackSeventeen' differs from the proprietary male parent 'Bulk A' (unpatented) in that 'DrisBlackSeventeen' plants are spiny whereas 'Bulk A' plants are spineless. Additionally, 'DrisBlackSeventeen' plants have higher vigor compared to 'Bulk A' plants.

'DrisBlackSeventeen' differs from Driscoll's commercial variety 'Sleeping Beauty' (U.S. Plant Pat. No. 13,758) in that 'DrisBlackSeventeen' has a semi-upright growth habit, a rounded to angular cross section of dormant cane, an upwards attitude of spine apex in relation to cane, and a medium ovate fruit shape in longitudinal section. In contrast, 'Sleeping Beauty' has an upright growth habit, an angular to grooved cross section of dormant cane, an outwards to downwards attitude of spine apex in relation to cane, and an elliptic fruit shape in longitudinal section.

'DrisBlackSeventeen' differs from the commercial variety 'Tupy' (unpatented) in that 'Tupy' has an earlier production curve as compared to that of 'DrisBlackSeventeen'.

What is claimed is:

1. A new and distinct variety of blackberry plant designated 'DrisBlackSeventeen' as shown and described herein.

* * * * *